United States Patent [19]
Dyke et al.

[11] Patent Number: 5,919,789
[45] Date of Patent: Jul. 6, 1999

[54] XANTHINES AND THEIR THERAPEUTIC USE

[75] Inventors: Hazel Joan Dyke; John Gary Montana, both of Cambridge, United Kingdom

[73] Assignee: Darwin Discovery Limited, United Kingdom

[21] Appl. No.: 08/971,857

[22] Filed: Nov. 17, 1997

[30] Foreign Application Priority Data

Nov. 15, 1996 [GB] United Kingdom .................. 9623859

[51] Int. Cl.⁶ .................... A61K 31/52; C07D 473/10; C07D 473/06; C07D 247/02
[52] U.S. Cl. .................. 514/263; 544/61; 544/118; 544/268; 544/270; 544/271; 544/272; 544/273
[58] Field of Search ................ 514/263; 544/61, 544/118, 269–273

[56] References Cited

U.S. PATENT DOCUMENTS

| | | | |
|---|---|---|---|
| 4,883,801 | 11/1989 | Nathanson | 514/263 |
| 5,719,279 | 2/1998 | Kufner-Muhl et al. | 544/61 |

FOREIGN PATENT DOCUMENTS

| | | |
|---|---|---|
| 0369744 | 11/1989 | European Pat. Off. . |
| 0389282 | 3/1990 | European Pat. Off. . |
| 0435811 | 12/1990 | European Pat. Off. . |
| 9205176 | 4/1992 | WIPO . |
| 9323401 | 11/1993 | WIPO . |
| 9400452 | 1/1994 | WIPO . |

*Primary Examiner*—Theodore J. Criares
*Attorney, Agent, or Firm*—Saliwanchik, Lloyd & Saliwanchik

[57] ABSTRACT

Compounds of the formula (i)

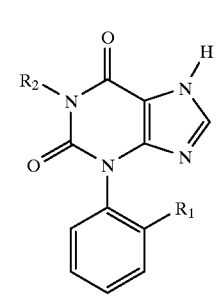

have therapeutic utility via inhibition of TNF or phophodiesterase.

6 Claims, No Drawings

XANTHINES AND THEIR THERAPEUTIC USE

FIELD OF THE INVENTION

The present invention relates to novel heterocyclic compounds and pharmaceutically-acceptable salts thereof, processes for their production and formulation and use as pharmaceuticals.

BACKGROUND OF THE INVENTION

Xanthine compounds such as theophylline, pentoxifylline and propentofylline have been widely used for the treatment of respiratory tract disease or brain dysfunction. Severe adverse reactions are frequently induced by the administration of these compounds. Examples of the adverse reactions are, for example, cardio-excitatory activity such as cardiopalmus or tachycardia; central activity such as convulsion or headache; and gastrointestinal activity such as nausea or emesis.

U.S. Pat. No. 4,883,801 discloses xanthine derivatives as pesticidal and pestistatic agents. Related xanthine derivatives have been disclosed as intermediates, without pharmacological activity, in EP-A-0369744, WO-A-92/05176, EP-A-0389282 and WO-A-94/00452.

EP-A-0435811 discloses xanthine derivatives as phosphodiesterase inhibitors. Further xanthines are disclosed in WO-A-9323401.

Phosphodiesterases (PDE) and Tumour Necrosis Factor (TNF), their modes of action and the therapeutic utilities of inhibitors thereof, are described in WO-A-9720833.

SUMMARY OF THE INVENTION

This invention is directed to the pharmaceutical use of a compound of formula (i) below to treat disease states, for example disease states associated with proteins which mediate cellular activity, for example by inhibiting tumour necrosis factor and/or by inhibiting phosphodiesterase IV. According to the invention, novel compounds are of formula (i):

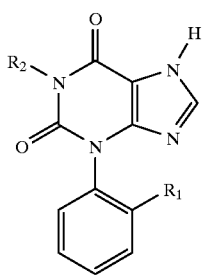

(i)

$R_1$ is alkyl (optionally substituted with one or more halogens), $NR_3R_4$, $CO_2R_4$, halogen, OH, alkoxy, CN, $NO_2$, $S(O)_nR_5$ or $COR_5$;

$R_2$ is alkyl, alkenyl, alkynyl or cycloalkyl;

$R_3$ is H, alkyl, cycloalkyl, cycloalkylcarbonyl, cycloalkylsulphonyl, alkylcarbonyl, alkoxycarbonyl, arylcarbonyl, heteroarylcarbonyl, heterocyclocarbonyl, alkylsulphonyl, arylsulphonyl, heteroarylsulphonyl, heterocyclosulphonyl, arylalkylcarbonyl, heteroarylalkylcarbonyl, heterocycloalkylcarbonyl, arylalkylsulphonyl, heteroarylalkylsulphonyl or heterocycloalkylsulphonyl;

$R_4$ is H, alkyl, cycloalkyl, arylalkyl, heteroarylalkyl or heterocycloalkyl;

$R_5$ is alkyl, cycloalkyl, aryl, heteroaryl, heterocyclo, arylalkyl, heteroarylalkyl or heterocycloalkyl; and n is 0–2;

and pharmaceutically-acceptable salts.

DESCRIPTION OF THE INVENTION

Suitable pharmaceutically-acceptable salts are pharmaceutically-acceptable base salts and pharmaceutically-acceptable acid addition salts. Certain of the compounds of formula (i) which contain an acidic group form base salts. Suitable pharmaceutically-acceptable base salts include metal salts, such as alkali metal salts for example sodium salts, or organic amine salts such as that provided with ethylenediamine.

Certain of the compounds of formula (i) which contain an amino group form acid addition salts. Suitable acid addition salts include pharmaceutically-acceptable inorganic salts such as the sulphate, nitrate, phosphate, borate, hydrochloride and hydrobromide and pharmaceutically-acceptable organic acid addition salts such as acetate, tartrate, maleate, citrate, succinate, benzoate, ascorbate, methane-sulphate, α-ketoglutarate, α-glycerophosphate and glucose-1-phosphate. The pharmaceutically-acceptable salts of the compounds of formula (i) are prepared using conventional procedures.

It will be appreciated by those skilled in the art that some of the compounds of formula (i) may exist in more than one tautomeric form. This invention extends to all tautomeric forms. It will be appreciated that the compounds according to the invention can contain one or more asymmetrically substituted carbon atoms. The presence of one or more of these asymmetric centers in a compound of formula (i) can give rise to stereoisomers, and in each case the invention is to be understood to extend to all such stereoisomers, including enantiomers, and diastereoisomers and mixtures including racemic mixtures thereof.

When used herein the term alkyl whether used alone or when used as part of another group includes straight and branched chain alkyl groups containing up to 6 atoms. Alkenyl means an aliphatic hydrocarbon group containing one or more carbon—carbon double bonds, which may be straight or branched having about 2 to about 10 carbon atoms. Alkynyl means an aliphatic hydrocarbon group containing one or more carbon—carbon triple bonds, which may be straight or branched having about 2 to about 10 carbon atoms. Cycloalkyl includes a non-aromatic cyclic or multicyclic ring system of about 3 to about 10 carbon atoms. Alkoxy means an alkyl-O-group in which the alkyl group is as previously described. Alkylcarbonyl means an alkyl-CO-group in which the alkyl group is as previously described. Aryl indicates an aromatic monocyclic or multicyclic carbocyclic group containing about 6 to 10 carbon atoms. Heteroaryl means about a 5 to about a 10 membered aromatic monocydic or multicyclic hydrocarbon ring system in which one or more of the atoms in the ring system is an element other than carbon, chosen from amongst nitrogen, oxygen or sulphur. Heterocyclo means about a 5 to about a 10 membered saturated or partially saturated monocyclic or multicyclic hydrocarbon ring system in which one or more of the atoms in the ring system is an element other than carbon, chosen from N, O and S; if desired, the N atom may be as N-oxide. Arylcarbonyl means an aryl-CO-group. Heteroarylcarbonyl means a heteroaryl-CO-group. Heterocyclocarbonyl means a heterocyclo-CO-group. Arylsulphonyl means an aryl-$SO_2$-group. Heteroarylsulphonyl means a heteroaryl-$SO_2$-group. Heterocyclosulphonyl means a heterocyclo-$SO_2$-group. Alkylsulphonyl means an alkyl-$SO_2$-group. Halogen means fluorine, chlorine, bromine or iodine.

"TNF mediated disease or disease states" means any and all disease states in which TNF plays a role, either by production of TNF itself, or by TNF causing another cytokine to be released, such as but not limited to IL-1 or IL-6. A disease state in which IL-1, for instance, is a major component, and whose production or action is exacerbated or secreted in response to TNF, would therefore be considered a disease state mediated by TNF. As TNF-β (also known as lymphotoxin) has close structural homology with TNF-α (also known as cachectin), and since each induces similar biologic responses and binds to the same cellular receptor, both TNF-α and TNF-β are inhibited by the compounds of the present invention and thus are herein referred to collectively as "TNF" unless specifically delineated otherwise.

This invention relates to a method for mediating or inhibiting the enzymatic activity or catalytic activity of PDE IV in a mammal in need thereof and for inhibiting the production of TNF in a mammal in need thereof, which comprises administering to said mammal an effective amount of a compound of Formula (i) or a pharmaceutically-acceptable salt thereof.

PDE IV inhibitors are useful in the treatment of a variety of allergic and inflammatory diseases, including: asthma, chronic obstructive airways disease, chronic pulmonary inflammation, chronic bronchitis, atopic dermatitis, atopic eczema, urticaria, allergic rhinitis, allergic conjunctivitis, vernal conjunctivitis, inflammation of the eye, allergic responses in the eye, eosinophilic granuloma, psoriasis, Bechet's disease, erythematosis, anaphylactoid purpura nephritis, joint inflammation, arthritis, rheumatoid arthritis and other arthritic conditions such as rheumatoid spondylitis and osteoarthritis, septic shock, ulcerative colitis, Crohn's disease, reperfusion injury of the myocardium and brain, chronic glomerulonephritis, endotoxic shock and adult respiratory distress syndrome. In addition, PDE IV inhibitors are useful in the treatment of diabetes insipidus and conditions associated with cerebral metabolic inhibition, such as cerebral senility, senile dementia (Alzheimer's disease), memory impairment associated with Parkinson's disease, depression and multi-infarct dementia. PDE IV inhibitors are also useful in conditions ameliorated by neuroprotectant activity, such as cardiac arrest, stroke and intermittent claudication. Additionally, PDE IV inhibitors could have utility as gastroprotectants. A preferred embodiment of the therapeutic methods of the present invention is the treatment of asthma.

The viruses contemplated for treatment herein are those that produce TNF as a result of infection, or those which are sensitive to inhibition, such as by decreased replication, directly or indirectly, by the TNF inhibitors of Formula (i). Such viruses include, but are not limited to HIV-1, HIV-2 and HIV-3, cytomegalovirus (CMV), influenza, adenovirus and the Herpes group of viruses, such as, but not limited to, Herpes zoster and Herpes simplex.

This invention more specifically relates to a method of treating a mammal, afflicted with a human immunodeficiency virus (HIV), which comprises administering to such mammal an effective TNF inhibiting amount of a compound of Formula (i) or a pharmaceutically-acceptable salt thereof.

The compounds of this invention may be also be used in association with the veterinary treatment of animals, other than humans, in need of inhibition of TNF production. TNF mediated diseases for treatment, therapeutically or prophylactically, in animals include disease states such as those noted above, but in particular viral infections. Examples of such viruses include, but are not limited to feline immunodeficiency virus (FIV) or other retroviral infection such as equine infectious anaemia virus, caprine arthritis virus, visna virus, maedi virus and other lentiviruses.

The compounds of this invention are also useful in treating parasite, yeast and fungal infections, where such yeast and fungi are sensitive to upregulation by TNF or will elicit TNF production in vivo. A preferred disease state for treatment is fungal meningitis.

The compounds of formula (i) are preferably in pharmaceutically-acceptable form. By pharmaceutically-acceptable form is meant, inter alia, of a pharmaceutically-acceptable level of purity excluding normal pharmaceutical additives such as diluents and carriers, and including no material considered toxic at normal dosage levels. A pharmaceutically-acceptable level of purity will generally be at least 50% excluding normal pharmaceutical additives, preferably 75%, more preferably 90% and still more preferably 95%.

Compounds of formula (i) may be prepared by the procedures described for corresponding xanthines, including interconversion, in WO-A-9636638. Any modifications that may be necessary, in view of having $R_2$ rather than $CHR_6Q$ as the target, will be evident to those skilled in the art.

It will be appreciated that where a particular stereoisomer of formula (i) is required, this may be obtained by conventional resolution techniques such as high performance liquid chromatography or the synthetic processes herein described may by performed using the appropriate homochiral starting material.

A compound of formula (i) or where appropriate a pharmaceutically-acceptable salt thereof and/or a pharmaceutically-acceptable solvate thereof, may be administered per se or, preferably, as a pharmaceutical composition also comprising a pharmaceutically-acceptable carrier.

Accordingly, the present invention provides a pharmaceutical composition comprising a compound of formula (i) or where appropriate a pharmaceutically-acceptable salt thereof and/or a pharmaceutically-acceptable solvate thereof, and a pharmaceutically-acceptable carrier.

The active compound may be formulated for administration by any suitable route, the preferred route depending upon the disorder for which treatment is required, and is preferably in unit dosage form or in a form that a human patient may administer to himself in a single dosage. Advantageously, the composition is suitable for oral, rectal, topical, parenteral administration or through the respiratory tract. Preparations may be designed to give slow release of the active ingredient.

The term parenteral as used herein includes subcutaneous injections, intravenous, intramuscular, intrastemal injection or infusion techniques. In addition to the treatment of warm-blooded animals such as mice, rats, horses, cattle, sheep, dogs, cats, etc, the compounds of the invention are effective in the treatment of humans.

The compositions of the invention may be in the form of tablets, capsules, sachets, vials, powders, granules, lozenges, suppositories, reconstitutable powders, or liquid preparations such as oral or sterile parenteral solutions or suspensions. Topical formulations are also envisaged where appropriate.

In order to obtain consistency of administration it is preferred that a composition of the invention is in the form of a unit dose.

Unit dose presentation forms for oral administration may be tablets and capsules and may contain conventional excipients such as binding agents, for example syrup, acacia, gelatin, sorbitol, tragacanth, or polyvinylpyrrolidone; fillers for example microcrystalline cellulose, lactose, sugar, maize-starch, calcium phosphate, sorbitol or glycine; tabletting lubricants, for example magnesium stearate; disintegrants, for example starch, polyvinylpyrrolidone, sodium starch glycolate or microcrystalline cellulose; or pharmaceutically-acceptable wetting agents such as sodium lauryl sulphate.

The solid oral compositions may be prepared by conventional methods of blending, filling, tabletting or the like. Repeated blending operations may be used to distribute the active agent throughout those compositions employing large quantities of fillers.

Such operations are of course conventional in the art. The tablets may be coated according to methods well known in normal pharmaceutical practice, in particular with an enteric coating.

Oral liquid preparations may be in the form of, for example, emulsions, syrups or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethylcellulose, aluminium stearate gel, hydrogenated edible fats; emulsifying agents, for example lecithin, sorbitan monooleate, or acacia, non-aqueous vehicles (which may include edible oils), for example almond oil, fractionated coconut oil, oily esters such as esters of glycerine, propylene glycol, or ethyl alcohol; preservatives, for example methyl or propyl p-hydroxybenzoate or sorbic acid; and if desired conventional flavouring or colouring agents.

Compositions may also suitably be presented for administration to the respiratory tract as a snuff or an aerosol or solution for a nebuliser, or as a microfine powder for insufflation, alone or in combination with an inert carrier such as lactose. In such a case the particles of active compound suitably have diameters of less than 50 microns, such as from 0.1 to 50 microns, preferably less than 10 microns, for example from 1 to 10 microns, 1 to 5 microns or from 2 to 5 microns. Where appropriate, small amounts of other anti-asthmatics and bronchodilators for example sympathomimetic amines such as isoprenaline, isoetharine, salbutamol, phenylephrine and ephedrine; corticosteroids such as prednisolone and adrenal stimulants such as ACTH may be included.

For parenteral administration, fluid unit dosage forms are prepared utilizing the compound and a sterile vehicle, and, depending on the concentration used, can be either suspended or dissolved in the vehicle. In preparing solutions the compound can be dissolved in water for injection and filter sterilised before filling into a suitable vial or ampoule and sealing.

Advantageously, adjuvants such as local anaesthetic, a preservative and buffering agents can be dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilisation cannot be accomplished by filtration. The compound can be sterilised by exposure to ethylene oxide before suspending in the sterile vehicle. Advantageously, a surfactant or wetting agent is included in the composition to facilitate uniform distribution of the compound.

The compositions may contain from 0.1% to 99% by weight, preferably from 10–60% by weight, of the active material, depending on the method of administration.

Compounds of formula (i), or if appropriate a pharmaceutically-acceptable salt thereof and/or a pharmaceutically-acceptable solvate thereof, may also be administered as a topical formulation in combination with conventional topical excipients.

Topical formulations may be presented as, for instance, ointments, creams or lotions, impregnated dressings, gels, gel sticks, spray and aerosols, and may contain appropriate conventional additives such as preservatives, solvents to assist drug penetration and emollients in ointments and creams. The formulations may contain compatible conventional carriers, such as cream or ointment bases and ethanol or oleyl alcohol for lotions.

Suitable cream, lotion, gel, stick, ointment, spray or aerosol formulations that may be used for compounds of formula (i) or if appropriate a pharmaceutically-acceptable salt thereof are conventional formulations well known in the art, for example, as described in standard text books such as Harry's Cosmeticology published by Leonard Hill Books, Remington's Pharmaceutical Sciences, and the British and US Pharmacopoeias.

Suitably, the compound of formula (i), or if appropriate a pharmaceutically-acceptable salt thereof, will compromise from about 0.5 to 20% by weight of the formulation, favourably from about 1 to 10%, for example 2 to 5%.

The dose of the compound used in the treatment of the invention will vary in the usual way with the seriousness of the disorders, the weight of the sufferer, and the relative efficacy of the compound. However, as a general guide suitable unit doses may be 0.1 to 1000 mg, such as 0.5 to 200, 0.5 to 100 or 0.5 to 10 mg, for example 0.5, 1, 2, 3, 4 or 5 mg; and such unit doses may be administered more than once a day, for example 2, 3, 4, 5 or 6 times a day, but preferably 1 or 2 times per day, so that the total daily dosage for a 70 kg adult is in the range of about 0.1 to 1000 mg, that is in the range of about 0.001 to 20 mg/kg/day, such as 0.007 to 3, 0.007 to 1.4, 0.007 to 0.14 or 0.01 to 0.5 mg/kg/day, for example 0.01, 0.02, 0.04, 0.05, 0.06, 0.08, 0.1 or 0.2 mg/kg/day, and such therapy may extend for a number of weeks or months.

When used herein the term "pharmaceutically-acceptable" encompasses materials suitable for both human and veterinary use.

The following Example illustrates the invention.

Intermediate 1

1-(2-Methylphenyl)-3-propylurea

2-Toluidine (32.1 g) was dissolved in toluene (500 ml) and propyl isocyanate (25.2 g) was added in one portion with stirring. The mixture was stirred for 1 h and then allowed to stand at room temperature for 6 h. The solid was collected by filtration and washed with toluene to provide the title compound (36.5 g).
mp131–134° C.

Intermediate 2

1-(2-Cyanoacetyl)-1-propyl-3-(2-methylphenyl)urea

A mixture of Intermediate 1 (27.53 g), cyanoacetic acid (13.37 g) and acetic anhydride (41 ml) was heated and stirred at 75° C. for 6.5 h. The resultant mixture was concentrated in vacuo to provide a thick oil. Trituration with ether provided the title compound (28.8 g).
mp 115–117° C.

Intermediate 3

6-Amino-1-(2-methylphenyl)-3-propyluracil

Triethylamine (9.09 g) was added to a stirred solution of Intermediate 2 (15.54 g) in dichloromethane (120 ml). After stirring for 1.25 h the resultant solid was collected by filtration and washed with dichloromethane to provide the title compound (13.25 g).
mp 226–228° C.

EXAMPLE 1

3-(2-Methylphenyl)-1-propylxanthine

A mixture of Intermediate 3 (7.12 g), formic acid (4.21 ml) and sodium nitrite (1.92 g) in formamide (163 ml) was heated at 60° C. for 10 minutes and then the temperature was increased to 100° C. Sodium dithionite (6.32 g) was added in portions over a period of 10 min with stirring. The temperature was raised to 190° C. and the mixture stirred at this temperature for 30 min. The reaction mixture was allowed to cool and extracted into chloroform. The chloroform solution was washed with water and then extracted with 2M sodium hydroxide solution. The basic extracts were washed with ether and then acidified with concentrated hydrochloric acid to give a solid which was filtered off and washed with water. Recrystallisation from ethyl acetate provided the title compound (3.48 g).
TLC $R_f$ 0.39 (ethyl acetate)
mp 221–226° C.

Assay methods

The assays used to confirm the phosphodiesterase IV inhibitory activity of compounds of formula (i) are standard assay procedures as disclosed by Schilling et al, Anal. Biochem. 216:154 (1994), Thompson and Strada, Adv. Cycl. Nucl. Res. 8:119 (1979) and Gristwood and Owen, Br. J. Pharmacol. 87:91P (1986).

Compounds of formula (i) have exhibited activity at levels consistent with those believed to be useful in treating phosphodiesterase IV-related disease states in those assays.

The ability of compounds of formula (i) to inhibit TNF production in human monocytes is measured as follows. Peripheral blood mononuclear cells are prepared from freshly taken blood by standard procedures. Cells are plated out in RPMI1640 +1% foetal calf serum in the presence and absence of inhibitors. LPS (100 ng/ml) is added and cultures are incubated for 22 h at 37° C. in an atmosphere of 95% air/5% $CO_2$. Supernatants are tested for TNFα by ELISA using commercially available kits.

In vivo activity in a skin eosinophilia model is determined by using the methods described by Hellewell et al, Br. J. Pharmacol. 111:811 (1994) and Br. J. Pharmacol. 110:416 (1993). Activity in a lung model is measured using the procedures described by Kallos and Kallos, Int. Archs. Allergy Appl. Immunol. 73:77 (1984), and Sanjar et al, Br. J. Pharmacol. 99:679 (1990).

An additional lung model, which allows measurement of inhibition of the early and late-phase asthmatic responses and also the inhibition of airway hyperreactivity, is described by Broadley et al, Pulmonary Pharmacol. 7:311 (1994), J. Immunological Methods 190:51 (1996) and British J. Pharmacol. 116:2351 (1995). Compounds of the invention show activity in this model.

We claim:

1. A compound of the general formula (i)

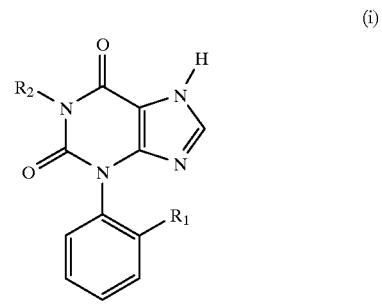

wherein $R_1$ is selected from the group consisting of alkyl, halogen substituted alkyl, $NR_3R_4$, $CO_2R_4$, halogen, OH, alkoxy, CN, $NO_2$, $S(O)_nR_5$, and $COR_5$;

$R_2$ is selected from the group consisting of alkyl, alkenyl, alkynyl or cycloalkyl;

$R_3$ is selected from the group consisting of H, alkyl, cycloalkyl, cycloalkylcarbonyl, cycloalkylsulphonyl, alkylcarbonyl, alkoxycarbonyl, arylcarbonyl, heteroarylcarbonyl, heterocyclocarbonyl, alkylsulphonyl, arylsulphonyl, heteroarylsulphonyl, heterocyclosulphonyl, arylalkylcarbonyl, heteroarylalkylcarbonyl, heterocycloalkylcarbonyl, arylalkylsulphonyl, heteroarylalkylsulphonyl, and heterocycloalkylsulphonyl;

$R_4$ is selected from the group consisting of H, alkyl, cycloalkyl, arylalkyl, heteroarylalkyl, and heterocycloalkyl;

$R_5$ is selected from the group consisting of alkyl, cycloalkyl, aryl, heteroaryl, heterocyclo, arylalkyl, heteroarylalkyl, and heterocycloalkyl; and n is 0–2;

or a pharmaceutically-acceptable salt thereof.

2. The compound, according to claim 1, wherein $R_1$ is alkyl.

3. The compound, according to claim 1, wherein $R_2$ is alkyl.

4. The compound, according to claim 1, which is 3-(2-methylphenyl)-1-propylxanthine.

5. The compound, according to claim 1, in the form of an enantiomer thereof.

6. A pharmaceutical composition for therapeutic use comprising a compound of claim 1 and a pharmaceutically-acceptable carrier or excipient.

* * * * *